(12) United States Patent
Burger et al.

(10) Patent No.: US 9,579,172 B2
(45) Date of Patent: Feb. 28, 2017

(54) METHOD OF MAKING A FACING FOR A DENTAL RESTORATION, FACING FOR A DENTAL RESTORATION, AND METHOD OF MAKING A DENTAL RESTORATION

(75) Inventors: Bernd K. Burger, Alling (DE); Holger Hauptmann, Sindelsdorf (DE)

(73) Assignee: 3M Innovative Properties Company, St. Paul, MN (US)

( * ) Notice: Subject to any disclaimer, the term of this patent is extended or adjusted under 35 U.S.C. 154(b) by 878 days.

(21) Appl. No.: 12/599,995

(22) PCT Filed: May 14, 2008

(86) PCT No.: PCT/US2008/063611
§ 371 (c)(1),
(2), (4) Date: Nov. 13, 2009

(87) PCT Pub. No.: WO2008/144342
PCT Pub. Date: Nov. 27, 2008

(65) Prior Publication Data
US 2010/0248189 A1    Sep. 30, 2010

(30) Foreign Application Priority Data
May 15, 2007    (EP) .................................... 07108206

(51) Int. Cl.
| A61C 13/083 | (2006.01) |
| A61C 13/09 | (2006.01) |
| A61C 5/00 | (2006.01) |
| A61C 5/10 | (2006.01) |
| A61C 13/00 | (2006.01) |

(52) U.S. Cl.
CPC .............. *A61C 13/09* (2013.01); *A61C 5/002* (2013.01); *A61C 5/10* (2013.01); *A61C 13/0003* (2013.01); *A61C 13/083* (2013.01)

(58) Field of Classification Search
USPC ................................... 264/16, 17, 18, 19, 20
See application file for complete search history.

(56) References Cited

U.S. PATENT DOCUMENTS

| 4,431,420 A | * | 2/1984 | Adair | ............................ 106/35 |
| 4,433,959 A | | 2/1984 | Faunce | |
| 4,650,418 A | | 3/1987 | Blair | |
| 4,828,117 A | | 5/1989 | Panzera | |
| 5,346,397 A | | 9/1994 | Braiman | |

(Continued)

FOREIGN PATENT DOCUMENTS

| CA | 2630250 | 5/2007 |
| DE | 19944130 | 4/2001 |

(Continued)

OTHER PUBLICATIONS http://www.glynwed.dk/files/File/FRIALIT-DEGUSSIT%20Over%20view%20catalogue%20english.pdf (retrieved Jun. 3, 2013).*

(Continued)

*Primary Examiner* — Timothy Kennedy

(57) ABSTRACT

A method of making a facing for a dental restoration. The method comprises the step of providing a facing precursor from which the facing is obtainable, and wherein the facing precursor is comprised of an open-celled material. The method provides for efficient manufacturing of dental restorations with optimized characteristics.

19 Claims, 7 Drawing Sheets

(56) References Cited

U.S. PATENT DOCUMENTS

| | | |
|---|---|---|
| 5,482,732 A | 1/1996 | Kramer |
| 5,745,229 A | 4/1998 | Jung |
| 5,902,441 A | 5/1999 | Bredt |
| 6,106,747 A | 8/2000 | Wohlwend |
| 6,121,175 A | 9/2000 | Drescher |
| 6,200,137 B1 | 3/2001 | Holand |
| 6,306,784 B1 | 10/2001 | Drescher |
| 6,322,728 B1 | 11/2001 | Brodkin |
| 6,354,836 B1 | 3/2002 | Panzera |
| 6,398,554 B1 | 6/2002 | Perot |
| 6,955,776 B1 | 10/2005 | Feenstra |
| 6,994,549 B2 | 2/2006 | Brodkin |
| 7,086,863 B2 | 8/2006 | Van der Zel |
| 7,452,836 B2 | 11/2008 | Apel |
| 2002/0082316 A1 | 6/2002 | Karmaker |
| 2002/0125592 A1 | 9/2002 | Schulman |
| 2004/0185422 A1 | 9/2004 | Orth |
| 2005/0023710 A1 | 2/2005 | Brodkin |
| 2005/0127544 A1* | 6/2005 | Brodkin et al. ............... 264/16 |
| 2006/0082033 A1 | 4/2006 | Hauptmann |
| 2006/0099552 A1 | 5/2006 | van der Zel |
| 2006/0106484 A1 | 5/2006 | Saliger |
| 2006/0257824 A1 | 11/2006 | Pfeiffer |
| 2007/0077534 A1 | 4/2007 | Saliger |
| 2007/0154868 A1 | 7/2007 | Scharlack |
| 2007/0212667 A1 | 9/2007 | Jung |
| 2008/0318189 A1 | 12/2008 | Brodkin |
| 2010/0221682 A1 | 9/2010 | Burger |

FOREIGN PATENT DOCUMENTS

| | | |
|---|---|---|
| DE | 60112245 | 3/2006 |
| DE | 102005034803 | 3/2006 |
| DE | 60020574 | 4/2006 |
| DE | 60023315 | 8/2006 |
| DE | 102006015014 | 10/2007 |
| EP | 431924 | 6/1991 |
| EP | 795311 | 9/1997 |
| EP | 1250895 | 10/2002 |
| EP | 1293174 | 3/2003 |
| EP | 1454596 | 9/2004 |
| EP | 1645663 | 4/2006 |
| EP | 1712534 | 10/2006 |
| EP | 1974688 | 10/2008 |
| EP | 1992302 | 11/2008 |
| EP | 2050417 | 4/2009 |
| EP | 2236121 | 10/2010 |
| WO | WO 94/19112 | 9/1994 |
| WO | WO 94/27517 | 12/1994 |
| WO | WO 03/066326 | 8/2003 |
| WO | WO 2004/073961 | 9/2004 |
| WO | WO 2006/120255 | 11/2006 |
| WO | WO 2007/028787 | 3/2007 |
| WO | WO 2007/060142 | 5/2007 |
| WO | WO 2008/009495 | 1/2008 |
| WO | WO 2008/103024 | 8/2008 |
| WO | WO 2009/052082 | 4/2009 |
| WO | WO 2009/070469 | 6/2009 |
| WO | WO 2010/074890 | 7/2010 |

OTHER PUBLICATIONS

Ebert, "Direct Inkjet Printing of Dental Prostheses Made of Zirconia", J. Dent. Res. 2009, vol. 88, No. 7, pp. 673-676.
Gbureck, "Preparation of Tricalcium Phosphate/calcium Pyrophosphate Structures Via Rapid Prototyping", J. Mater. Sci., Mater. Med., 2008, vol. 19, pp. 1559-1563.
Moon, "Ink-jet Printing of Binders for Ceramic Components", J. Am. Ceram. Soc., 2002, vol. 85, No. 4, pp. 755-762. ISSN 0002 7820.
Seitz, "Three-Dimensional Printing of Porous Ceramic Scaffolds for Bone Tissue Engineering", J. Biomed. Mater. Res. Part B: Appl. Biomater., 2005, vol. 74B, pp. 782-788.
Wang, "Solid Freeform Fabrication of Permanent Dental Restorations Via Slurry Micro-extrusion", J. Am. Ceram. Soc., 2006, vol. 89, No. 1, pp. 346-349.
European Search Report for PCT Application No. 07108206, 5 pgs.
Written Opinion of the ISA for International Application No. PCT/US2008/063611, 9 pgs.
International Search Report for PCT/US2008/063611, 6 pgs.
International Search Report for PCT/US2008/079788, 6 pgs.
Written Opinion of the ISA for International Application No. PCT/US2008/079788, 10 pgs.
European Search Report for PCT Application No. 07118476, 10 pgs.
Search Report for GB App. No. GB0822751, 4 pgs.
Written Opinion of the ISA for International Application No. PCT/US2009/066167, 5 pgs.
International Search Report for PCT/US2009/066167, 4 pgs.

* cited by examiner

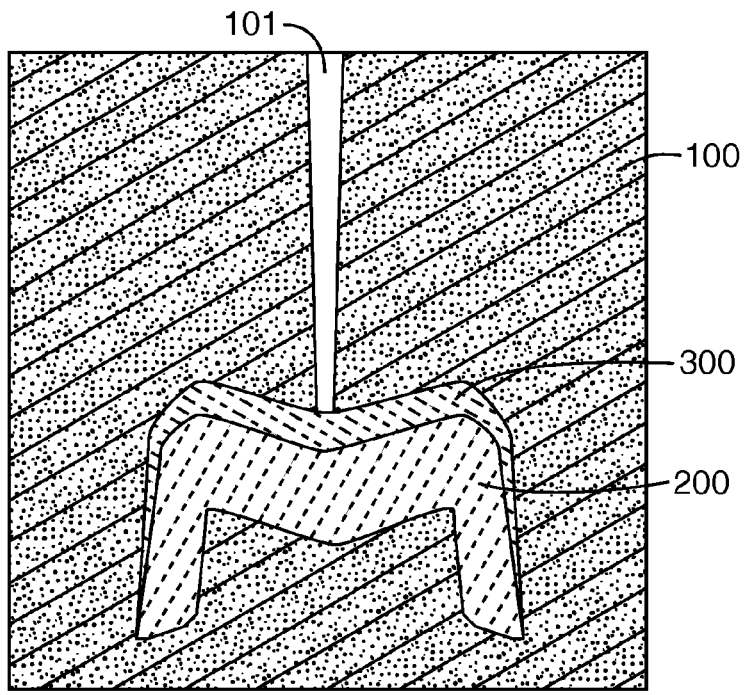
Fig. 1
PRIOR ART
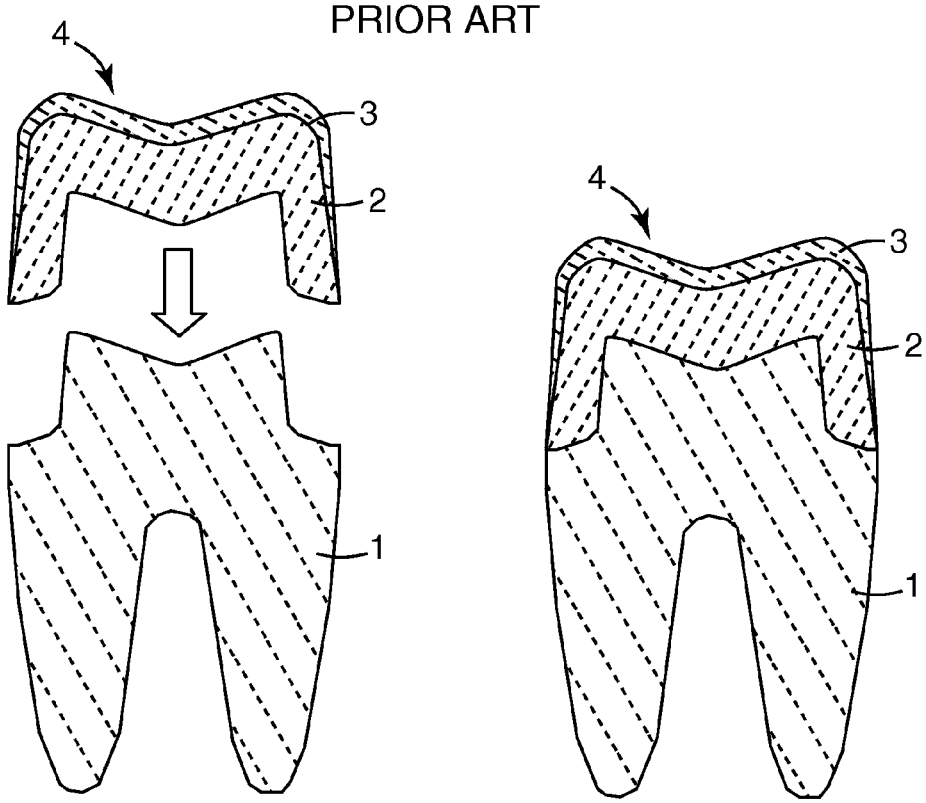
Fig. 3a          Fig. 3b

METHOD OF MAKING A FACING FOR A DENTAL RESTORATION, FACING FOR A DENTAL RESTORATION, AND METHOD OF MAKING A DENTAL RESTORATION

CROSS REFERENCE TO RELATED APPLICATIONS

This application is a national stage filing under 35 U.S.C. 371 of PCT/US2008/063611, filed May 14, 2008, which claims priority to EP Application No. 07108206.9, filed May 15, 2007, the disclosure of which is incorporated by reference in its/their entirety herein.

FIELD OF THE INVENTION

The invention generally relates to dental restorations, and in more particular to methods for making facings for dental restorations, such as bridges, inlays, onlays, crowns, or abutments, for example, from ceramic materials.

BACKGROUND OF RELATED ART

In the field of dentistry, restoration of a patient's tooth or teeth that have, for example, been affected by caries generally includes the replacement of the natural tooth substance by an artificial substance. For larger restorations, pre-finished dental restorations or prostheses are commonly used to replace at least a part of the tooth or teeth.

Dental restorations or prostheses are often made as a two or more component configuration, with the individual components providing different characteristics for the restoration. For example, a frame may provide excellent structural support, and a facing may provide excellent aesthetics. The frame generally is a supporting structure for the dental restoration that provides mechanical stability and usually comprises an interface by which the restoration can be affixed to a prepared tooth of a patient. The facing provides for pleasing aesthetic characteristics that gives the restoration the shape and appearance of natural teeth. In addition, both the frame and the facing are shaped to fit well with the adjacent and opposed teeth in a patient's mouth.

In the recent years ceramic materials have been widely used for making high-quality dental restorations because of their good physical, aesthetic and biological properties.

These restorations are often manufactured by an automated process, which typically includes:
- capturing data representing the shape of a patient's teeth, for example by scanning a plaster model of the patient's teeth or alternatively by scanning the actual teeth in the patient's mouth;
- designing the shape of a frame based on the captured data using software, such as computer-aided design (CAD) software; and
- manufacturing the frame to correspond to the designed shape, for example, by an automated Computer Numerical Controlled (CNC) machine.

There are approaches to integrating the steps of capturing, designing and manufacturing in a Computer Integrated Manufacturing (CIM) system. An exemplary CIM system for making frames for dental restorations is available from 3M ESPE AG (Seefeld, Germany) under the trade designation LAVA™.

Although such CIM systems would allow the manufacture of an integrated dental restoration (frame and facing together, in the example mentioned above), it is difficult to provide a single ceramic material that provides both the necessary structural durability and good aesthetics. Therefore the CIM system is normally used to manufacture the frame from a ceramic material that provides the required mechanical durability without regard to its aesthetic properties, after which a final layer or facing is applied to the frame to provide the necessary aesthetic properties. A facing of this type is very often manually prepared by skilled dental technicians, for example by manually applying several layers of a polymeric material or a glass-ceramic material, to provide the appropriate color, translucency, and other properties.

Another common method for manually preparing a facing is the "press over" technique shown in FIG. 1. A frame 200 is manufactured as described above, and manually covered with a wax layer or "wax-up" 300 with an outer surface that corresponds to the desired final shape of the tooth. That wax-up is used to form a pattern for a mold 100. The mold 100 is then heated in a furnace so that the wax is burned off, and the frame 200 remains as a core in the mold. The space between the core and the interior of the mold is then filled with a molten glass-ceramic material that is, for example, obtained from melting a ceramic pellet in channel 101 or previously molten and poured into the channel 101, where it flows around the frame and fuses with the frame to form the facing. The restoration may then be removed from the mold, polished as necessary, and provided to the dentist for application to the patient's tooth.

Other methods of preparing dental restorations are described, for example, in DE-A1-10 2005 034 803, and DE-A1-199 44 130.

Although the current approaches for manufacturing of dental restorations may provide a variety of advantages, there is still a desire for a method of manufacturing an entire high-quality dental restoration in a cost efficient manner.

SUMMARY OF THE INVENTION

In a first aspect the present invention provides a method of making a facing for a dental restoration. The method comprises the step of:
  providing a facing precursor from which the facing is obtainable, and wherein the facing precursor is comprised of an open-celled material.

The open-celled material is preferably a pre-sintered material. Preferably the facing is obtainable by sintering the facing precursor.

In an embodiment of the invention the facing precursor is provided by the steps of:
  providing a blank of an open-celled pre-sintered material, and
  forming the facing precursor from the blank.

In another embodiment of the invention the method further comprises the step of:
  sintering the facing precursor to form the facing.

The term "facing" within the meaning of this invention refers to the aesthetic part of a dental restoration, meaning the part comprising an outer surface of the finished restoration. The facing is further adapted to be applied to a frame which forms another part of the dental restoration, and the dental restoration is in turn applied to a tooth. The facing is preferably arranged at those parts of the frame that are likely to be visible in a patient's mouth, or that in particular functionally co-operate with the adjacent or opposed teeth of a patient, for example.

Typically a blank of the open-celled pre-sintered material is provided by the steps of:

pressing an amount of particles together to form a material body, and
pre-sintering the material body at a temperature of between 500° C. and 750° C. to form the blank.

In an embodiment of the invention sintering transforms the open-celled material into a sintered material that forms the facing. Preferably the facing precursor has a first material density and the facing has a second material density. In particular, the first and second densities may correspond to the densities of the materials the facing precursor and the facing, respectively, are comprised of Preferably the second material density is higher than the first material density.

In a preferred embodiment of the invention, sintering the facing precursor comprises, consists essentially of, or consists of heating the facing precursor. Sintering may, for example, comprise heating the material to a temperature of between about 700° C. to 1100° C. for a time of between about 1 to 3 hours. The facing precursor may further be sintered at an atmospheric pressure of between about 25 and 50 mbar. Sintering typically includes the densification of a porous material to a less porous material (or a material having less cells) having a higher density, in some cases sintering may also include changes of the material phase composition may occur (for example, a partial conversion of an amorphous phase toward a crystalline phase). A porous material sometimes refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field.

In an embodiment of the invention the facing precursor is dimensionally proportional to and larger than the facing, where the facing precursor is proportionally enlarged relative to the facing by a magnification factor of between about 1.05 and about 2.2, in more particular between about 1.05 and about 1.4, more preferably between about 1.12 and about 1.17 and preferably about 1.16.

The term "proportionally enlarged" means that each of the three dimensions of an enlarged object is enlarged relative to the corresponding dimension of the original object by preferably substantially the same magnification factor. Further, "proportionally enlarged" may include tolerances of the magnification factor in each dimension so that each of the three dimensions of the enlarged object may be enlarged relative to the corresponding dimension of the original object by three individual magnification factors with at least two of the individual magnification factors being different from each other by about 1% to about 5%.

Typically sintering results in the facing precursor shrinking proportionally. The shrinkage factor typically corresponds to the absolute value of the magnification factor. The facing therefore preferably has proportionally reduced dimensions relative to the facing precursor and the ratio of corresponding dimensions of the facing precursor and the facing is preferably between about 1.05:1 and about 2.2:1, in more particular between about 1.05:1 and about 1.4:1, more preferably between about 1.12:1 and about 1.17:1 and preferably about 1.16:1.

The term "proportionally reduced" means that each of the three dimensions of a shrunken object is reduced relative to the corresponding dimension of the original object by preferably substantially the same shrinkage factor. Further, "proportionally reduced" may include tolerances of the shrinkage factor in each dimension so that each of the three dimensions of the shrunken object may be reduced relative to the corresponding dimension of the original object by three individual shrinkage factors with at least two of the individual shrinkage factors being different from each other by about 1% to about 5%.

In another embodiment of the invention, providing the facing precursor includes removing material from a blank to form a facing precursor. Material may be removed from the blank by machining, for example, by grinding, milling, or a combination of both. Preferably the removal of material is performed by milling the shape of the facing precursor from the blank. The removal of material from a pre-sintered material takes relatively little effort relative to material removal from the same material after it has been sintered, because the pre-sintered material has a relatively low strength compared to sintered material. As a result, milling (rather than grinding) can be used to remove material from a blank, which is usually faster and more cost effective.

A blank may have a size of between about 20 mm and about 30 mm in two dimensions, for example may have a diameter in that range, and a may be of a certain length in a third dimension. A blank for making single crowns may have a length of between about 15 mm and about 30 mm, and a blank for making bridges may have a length of between about 40 mm and about 80 mm. A typical size of a blank as it is used for making single crowns has a diameter of about 24 mm and a length of about 19 mm. Further, a typical size of a blank as it is used for making bridges has a diameter of about 24 mm and a length of about 58 mm.

In a further embodiment the method comprises the steps of:
  forming an exterior surface of the facing precursor based on a virtual model of an exterior surface of the dental restoration; and
  forming an interior surface of the facing precursor based on a virtual model of an exterior surface of a frame.

A virtual model is typically a dataset adequate to define a three-dimensional surface, for example a dataset usable with CAD software. The exterior surface of the dental restoration may be designed with CAD software. Designing the exterior surface of the dental restoration may include the use of standard surfaces obtained from a database, for example loaded from the database into the CAD software. Accordingly, the method of the invention may comprise the step of modeling the exterior surface of the dental restoration on a CAD system, and modeling may include the use of data from a database that includes standard surfaces.

In an embodiment of the invention forming the exterior surface of the facing precursor includes at least one procedure selected from scanning a patient's tooth, scanning a temporary restoration, and scanning a model of a patient's tooth. For example, the shape of a plaster model of a patient's teeth obtained from a dental impression may be captured by a scanner for scanning three-dimensional objects, for example one available from 3M ESPE AG, Seefeld, Germany under the designation LAVA™ Scan ST.

The shape of the plaster model thus may be transformed into a scan model of the patient's teeth, including the tooth to be restored. To the extent the tooth or teeth to be restored are preserved and therefore available at the plaster model the shape of those tooth or teeth maybe used to determine a part of the shape of the exterior surface of the dental restoration. Therefore an appropriate part of the scan model may be used as a partial virtual model of the exterior surface of the dental restoration. The other part of the virtual model which is not obtainable from scanning the plaster model may be added by design, for example by use of a CAD software as described.

The exterior surface of the dental restoration may also be largely or entirely designed, for example, in case large parts of the tooth or teeth are not available at the plaster model because tooth substance has been removed to prepare the tooth surface for receiving the restoration. To insure that the restoration that is applied to the patient's tooth or teeth fits and works well, the design of the exterior surface of the dental restoration is preferably performed in view of the size, shape, and location of teeth that adjoin, cooperate with, or oppose the dental restoration. For example, the occlusal surfaces of an opposed tooth should readily mate with the occlusal surfaces of the restored tooth, which can be arranged by the appropriate design of the dental restoration in view of the opposed tooth or teeth. In the alternative, a restoration model representing the final shape of the dental restoration may be applied on the plaster model. As a result, the desired exterior surface of the dental restoration may be determined directly from the restoration model, and therefore can be directly obtained from scanning the plaster model including the restoration model. The restoration model may for example be a wax model which is manually shaped while on the plaster model of the remainder of the patient's teeth.

The exterior surface of the frame may be obtained by scanning a pre-finished frame, or by retrieving data from a CAD software or system with which the frame has been designed.

In another embodiment the method of the invention further comprises the step of mating the facing precursor with a frame to form a dental restoration precursor. For example, the facing precursor may be placed with its interior surface on an exterior surface of the frame. The interior surface of the facing precursor may be a proportionally or similarly dimensioned counterpart to the exterior surface of the frame, and more specifically the interior surface of the facing precursor may be a proportionally enlarged counterpart of the exterior surface of the frame, to permit the former to fit over the latter with any appropriate clearance. Preferably the facing precursor and the frame are fitted with ceramic slurry arranged between mated surfaces of the frame and the facing precursor. Such ceramic slurry typically comprises a powdery glass ceramic material, for example of the type used for the facing, which is mixed with water. The ceramic slurry may fill a clearance between mated surfaces of the facing precursor and the frame. The ceramic slurry may further provide for compensating tolerances within such clearance. In case a dental restoration precursor formed by use of ceramic slurry is sintered the ceramic slurry typically dries during sintering and the remaining particles fuse and form an intermediate layer between the facing and the frame. The ceramic slurry may further comprise an organic or a polymeric binder to provide a good adhesion of the intermediate layer with adjoining surfaces, and may provide a certain elasticity of the intermediate layer. Such elasticity may, for example, help to make a dental restoration more durable, in particular to help prevent a facing from loosening from the frame. The facing precursor and the frame may also be fitted without an additional substance, like ceramic slurry or the like, arranged between one another.

In a further embodiment the method further comprises the step of heating the dental restoration precursor. Preferably by heating of the dental restoration precursor the facing precursor is sintered. Heating of the dental restoration precursor may further include sintering the frame. For example, the facing precursor may be combined with a frame of a presintered material or with a frame of an already sintered material to form the dental restoration precursor. Therefore the facing precursor may be sintered onto a previously sintered frame, or the facing precursor and the frame may be sintered in one continuous process. Heating of the dental restoration precursor may fuse a surface of the facing to a surface of the frame. For example, if a frame of a pre-sintered material is used, the frame and the facing precursor may be sintered generally simultaneously or in a continuous process with the frame and the facing precursor fusing at their mating or contacting surfaces. Preferably the frame is made of a sintered material (a material generally free of cells, or at least closed-celled), for example a sintered or casted material, so that the facing precursor is sintered and with its interior surface fuses the mated exterior surface of the sintered frame. The use of a frame of sintered material, or a frame that does not require sintering at all, may be advantageous if the material used for the facing precursor has a lower sintering temperature than the material used for the frame, because it allows sintering of the facing precursor at the lower temperature. This helps to avoid having the material of the facing precursor become too soft, and may therefore result in better dimensional accuracy of the finished facing. Further, because the frame due to its higher sintering temperature remains substantially solid and substantially maintains its shape, it mechanically supports the softened facing precursor and thereby helps to achieve better dimensional accuracy of the finished facing and the finished dental restoration.

In another embodiment the method of the invention further comprises the step of at least partially glazing the facing. This may be advantageous to achieve a good optical appearance of the dental restoration and/or to render the dental restoration more durable.

A second aspect of the invention is related to a facing precursor for making a facing for a dental restoration. The facing precursor comprises an open-celled pre-sintered material. The facing precursor may also consist essentially of, or consist of, an open-celled pre-sintered material.

Preferably the facing precursor comprises or consists essentially of a glass or a glass ceramic material.

In an embodiment the facing precursor can be sintered to form a facing having a higher material density than the facing precursor. Preferably the facing precursor has a shape that corresponds to a proportional enlargement of the facing with a magnification factor of preferably between about 1.05 and about 2.2, in more particular between about 1.05 and about 1.4, more preferably between about 1.12 and about 1.17 and preferably about 1.16.

The facing precursor may comprise an interior surface corresponding to a proportionally dimensioned counter-surface to an exterior surface of a frame. The interior surface of the facing precursor may be scaled so that it matches the exterior surface of the frame when the facing precursor has been sintered.

In a preferred embodiment the interior surface of the facing precursor substantially corresponds to a counter-surface of an exterior surface of a frame, meaning that the interior surface of the facing precursor may substantially correspond to a negative exterior surface of the frame. During sintering, the material of the facing precursor would shrink toward the interior surface of the facing precursor with the interior surface generally maintaining its shape.

A third aspect of the invention is related to a facing for a dental restoration. The facing comprises a sintered material, wherein the sintered material is obtained or obtainable from sintering a facing precursor.

In a preferred embodiment the facing has a color within the range of colors of human teeth. The facing may be shaded in a manner so as to make the dental restoration resemble natural teeth, or it may be shaded so that the dental restoration when placed in a patient's mouth optically matches the natural tooth or teeth adjoining the dental restoration. Further, the facing preferably has a translucency similar of human teeth. The facing may comprise materials having different colors and a certain degree or certain degrees of translucency, for example, to provide an optical appearance resembling that of natural teeth.

A fourth aspect of the invention is related to a dental restoration, comprising a frame and a facing according to the invention. Preferably, the frame and the facing are attached to one another, for example fused at their mating or adjoining surfaces.

In a fifth aspect the invention is related to the use of a pre-sintered material to form a facing precursor for making a facing for a dental restoration. Preferably the pre-sintered material is an open-celled material, preferably an open celled ceramic material. Generally the use of a pre-sintered material may facilitate machining, rather than grinding, because the pre-sintered material has a relatively low material strength. Further, an open-celled material may provide for applying a facing to a frame substantially without trapping air and therefore may provide for good durability of the dental restoration.

In a sixth aspect the invention is directed to a method of machining a facing precursor for making a facing, comprising the step of controlling a CNC machine based on data related to the shape of the facing precursor which are obtained from a CAD system, wherein the facing precursor is proportionally enlarged with respect to the facing. Preferably machining includes, substantially consists of, or consists of milling.

The sintered material referred to in this specification preferably has a material density in a range of 2 g/cm$^3$ to 2.7 g/cm$^3$, and the pre-sintered material preferably has a material density in a range of 30% to 92% of the material density of the sintered material. Preferably the material density of the pre-sintered material is in a range of 40% to 60% of the material density of the sintered material, and more preferably in a range of 45% to 55%.

In particular, the facing referred to in this specification preferably has a material density in a range of 2 g/cm$^3$ to 2.7 g/cm$^3$, and the facing precursor preferably has a material density in a range of 30% to 92% of the material density of the facing. Preferably the material density of the facing precursor is in a range of 40% to 60% of the material density of the facing, and more preferably in a range of 45% to 55%.

For example, the material density of the facing precursor (or the pre-sintered material) may be in a range of 0.6 g/cm$^3$ to 1.84 g/cm$^3$ and the facing (or the sintered material) obtained from it may have a material density of about 2 g/cm$^3$. In another example the material density of the facing precursor (or the pre-sintered material) may be in a range of 0.81 g/cm$^3$ to 2.5 g/cm$^3$ and the facing (or the sintered material) obtained from it may have a material density of about 2.7 g/cm$^3$. The facing precursor (or the pre-sintered material) may generally have a material density in a range of 0.6 g/cm$^3$ to 2.5 g/cm$^3$.

Typically the difference between the density of the facing precursor and the density of the facing (or the pre-sintered material and the sintered material, respectively) is a result of the presence of a higher amount of cells within the facing precursor (or the pre-sintered material) than in the facing (the sintered material).

In an embodiment the pre-sintered material may be wax impregnated, meaning that wax at least partially fills the cells of the pre-sintered material. A wax impregnation improves stability of the material blank in order to prevent breakage of the blank during milling. In more detail, the wax impregnation dampens vibrations of the blank during milling or reduce dust. During the sintering process of the facing, the impregnated wax is typically burned off or melted.

The average size of the particles forming the pre-sintered material as referred to in this specification is typically in a range of about 10 μm to about 60 μm, and preferably about 30 μm. The distribution of the particle size may be for example:
  10% of the particles smaller than about 3 μm;
  50% of the particles smaller than about 26 μm; and
  90% of the particles smaller than about 71 μm.

In more particular the average particle size which the pre-sintered material referred to in this specification is comprised of may be about 20 μm, for example according to a particle size distribution in which:
  10% of the particles are smaller than about 1.2 μm;
  50% of the particles are smaller than about 10 μm; and
  90% of the particles are smaller than about 45 μm.

The volume of the cells in the pre-sintered material relative to the total volume of the pre-sintered material as referred to in this specification is typically in a range of about 20% to about 40%, and more preferably in a range of about 30% to about 38%.

The facing and the facing precursor as referred to in this specification preferably comprise a glass or glass ceramic material or may consist essentially of, or consist only of, a glass or glass ceramic material. The glass or glass ceramic material is preferably selected to be compatible for use in human bodies. Furthermore, the glass ceramic material is preferably selected to provide good aesthetic appearance for the dental restoration, in particular when combined with a frame. An exemplary formulation for a glass or glass ceramic as it may be used with the present invention comprises 60% to 70% by weight of silica, 9% to 13% by weight of alumina, 5% to 10% by weight of potassium-oxide, 9% to 13% by weight of sodium-oxide, 0% to 1% by weight of lithium-oxide, 2% to 5% by weight of calcia, 1% to 2% by weight of barium-oxide, 0% to 1% by weight of zirconium oxide and 0% to 1% cerium-oxide or cerium-fluoride.

Glass or glass ceramic materials which may, for example, be used for manufacturing a blank and/or a facing precursor are generally available under the designations:
  "VM 9" from Vita Zahnfabrik, Bad Sackingen, Germany;
  "Cerabien Zr" from Noritake Inc., Japan;
  "Vintage" from Shofu, Japan; and
  "ZIROX" from Wieland GmbH &Co. KG, Pforzheim, Germany.

The structure of a glass, a glass ceramic or a ceramic material as referred to in this specification may be categorized as "open-celled", "closed-celled" and "generally free of cells". The material structure categories "open-celled" and "closed-celled" have been determined for different porosities that have been measured at different material samples using mercury porosimetry according to DIN 66133. The porosity or open porosity was measured using a mercury porosimeter in accordance with DIN 66133 as available under the designation "Poremaster 60-GT" from Quantachrome Inc., USA. To obtain samples having such different porosities the samples have been pre-sintered to different degrees as described in the following.

The samples were uniaxially pressed from a powder of a reference glass ceramic material as specified below. The pressed samples had a pressed density which was in the range of about 1.34 g/cm$^3$ and about 1.42 g/cm$^3$. Each pressed sample was pre-sintered at ambient pressure of about 101.3 kPa in a process that comprised the steps of:

(1) exposing the sample to a temperature that was increased from room temperature of about 23° C. to about 540° C. at a heating rate of about 10 Kelvin per minute;
(2) exposing the sample to the temperature of about 540° C. for a dwell time period of about 30 minutes;
(3) exposing the sample to a temperature that was increased from the temperature of about 540° C. to a maximum temperature $T_{max}$ (as specified in the table) at a heating rate of about 10 Kelvin per minute; and
(4) exposing the sample to the temperature of about the maximum temperature $T_{max}$ for a dwell time period of about 30 minutes.

The reference glass ceramic material was a powder of a commercially available glass ceramic material that comprised 55% to 75% by weight of silicon oxide, 8% to 22% by weight of aluminum oxide, 0% to 8% by weight of boron oxide, 3% to 12% by weight of potassium oxide, 4% to 12% by weight of sodium oxide, 0.01% to 5% by weight of strontium oxide, 0.1% to 2% by weight of cerium oxide, 0.01% to 2% by weight of tin oxide, 0% to 3% by weight of zinc oxide, 0% to 4% by weight of phosphor oxide, 0% to 3% by weight of calcium oxide, 0% to 3% by weight of lithium oxide, and 0% to 1% by weight of fluoride. The density of the used glass ceramic material was about 2.5 g/cm$^3$ and had a glass transition temperature of about 550° C.

In the way described seven different material samples were prepared which are specified in Table 1, referenced as sample no. 1 to 7. The table shows the maximum temperature at which the individual samples were pre-sintered. Further the table represents measuring data of the sample volume, the sample weight and the open porosity of the individual samples. The open porosity was measured by mercury porosimetry according to DIN 66133. The sample volume was determined based on the overall outer dimensions of the individual samples. The sample density was calculated from the measured sample volume and the sample weight. The total volume of glass ceramic material was calculated from the ratio between the sample density and the density of the used glass ceramic material (2.5 g/cm$^3$). The total volume of cells in the sample was assumed to be the remainder of the sample volume (100% minus the total volume of glass ceramic material).

TABLE 1

| Sample no. | $T_{max}$ [° C.] | sample volume [cm$^3$] | sample weight [g] | sample density [g/cm$^3$] | total volume of glass ceramic material | total volume of cells | open porosity (acc. to mercury porosimetry DIN 66133) | Material structure |
|---|---|---|---|---|---|---|---|---|
| 1 | 560 | 6.11 | 8.76 | 1.43 | 57.3% | 42.7% | 32.9% | open-celled |
| 2 | 580 | 5.35 | 8.70 | 1.63 | 65.0% | 35.0% | 23.9% | open-celled |
| 3 | 600 | 5.07 | 8.74 | 1.72 | 68.9% | 31.1% |  | open-celled |
| 4 | 620 | 4.38 | 8.77 | 2.00 | 80.0% | 20.0% |  | open-celled |
| 5 | 640 | 4.05 | 8.77 | 2.17 | 86.6% | 13.4% | 6.1% | open-celled |
| 6 | 660 | 3.73 | 8.76 | 2.35 | 94.0% | 6.0% |  | closed-celled |
| 7 | 680 | 3.62 | 8.73 | 2.41 | 96.4% | 3.6% |  | closed-celled |

The term "open-celled" therefore preferably relates to an "open porosity" according to the mercury porosimetry as defined in DIN 66133 of between about 6% and about 35%, in particular of between about 15% and about 35%, and in more particular of between about 30% and about 35%.

Certain metals and/or alloys may also be used to make a frame as it may be used with the present invention as shown in table 2.

TABLE 2

| Supplier | Alloys with high fraction of noble metals | Alloys with reduced fraction of noble metals | Titanium | Palladium based alloys | CrCoMo based alloys |
|---|---|---|---|---|---|
| Wieland Hafner | Porta ® PK Orplid ® Universal | Porta ® SMK |  | Simidur ® S2 |  |
| Bego Dentaurum |  |  | rematitan ® M |  | Wirobond ® 280 Remanium ® CD |
| DeguDent ® | Degudent ® G | Degudor ® |  |  |  |

In particular, the term "ceramic" is intended to include translucent ceramic. Ceramics which are not naturally the same color as human teeth may be made shaded accordingly by compounding with pigments.

The facing as it is referred to in this specification may be substantially free of cells, however may comprise up to about 16 cells per mm$^2$ Preferably, the facing may comprise about 4 to about 8 cells per mm$^2$. The cells preferably have a diameter of less that about 150 µm, and more preferably a diameter of less than about 100 µm and most preferably a diameter of less than about 40 nm. In a particular embodiment the facing has less than about 16 cells per mm$^2$ with a diameter of less than about 150 μm, wherein not more than about 6 cells have a diameter of between about 40 and about 150 μm. The unit "cells per mm$^2$" is related to the number of cells present on a cross section according to the test method as defined in DIN 13925.

The raw breaking resistance or bending strength of the pre-sintered material or the facing precursor as referred to in this specification is preferably in a range of about 10 to about 15 MPa, more preferably in a range of about 11 to about 13 MPa, and preferably about 12 MPa according to the "punch on three ball test" as specified in ISO 6872.

The bending strength of the sintered material or the facing as referred to in this specification is preferably in a range of about 50 to about 400 MPa, in more particular in a range of about 50 to about 120 MPa according to the "punch on three ball test" as specified in ISO 6872.

The sintered material may be selected to provide a certain translucency. Typically the translucency is specified by the opacity of a material relative to daylight. Typical ranges of the opacity of the sintered material or the facing are 50% to 60% (typically corresponding to natural dental enamel), 60% to 80% (typically corresponding to natural dentine) and 80% to 90% (typically corresponding to natural opaque dentine).

A frame as referred to in this specification may be made of a pre-sintered material, a sintered material, or another suitable material. For example the frame may be casted from metal or a ceramic material, or may be machined from metal or ceramic material. Preferably the frame is made of a sintered ceramics material, for example a ceramic comprising zirconium oxide. However, the frame may also be made of metal or alloy. The material the frame is made of typically provides relatively good mechanical stability. In particular the frame may be made of a ceramic material comprising between 90 and 99% by weight zirconium oxide, and preferably 91 to 97.25% by weight zirconium oxide. The ceramic material of the frame may further comprise 0-1% by weight aluminium oxide. The ceramic material of the frame may also be based on aluminium oxide, meaning the ceramic material may comprise 90 to 99% by weight aluminium oxide and 0 to 1% by weight zirconium oxide. Further the ceramic material of the frame may comprise 0-10% by weight of at least one of hafnium oxide, yttrium oxide and oxides from gallium, germanium, and indium. The ceramic material of the frame may also comprise 0.0005 to 1.5% by weight of colouring additives, selected from the group consisting of the oxides $Fe_2O_3$, $Er_2O_3$ and/or $MnO_2$. The ceramic material of the frame is preferably selected to be compatible for use in human bodies.

The facing provided by the invention is advantageous in comparison to conventionally prepared facings because it is more homogeneous and comprises less imperfections or defects. Defects may for example occur at the mating area of the facing and the frame. This is because the facing is typically manufactured under standardized manufacturing conditions and from a material having a substantially homogeneous structure, in contrast to having a dental technician manually layering a facing. Furthermore, with the invention, an existing milling system can be used not only to manufacture the frame but also the facing. This substantially reduces the time needed to prepare a dental restoration, and also provides the synergistic effect that data of the CAD/CAM system used for making the frame are also useable in the design and manufacture of the facing. Making a facing of an open-celled, for example pre-sintered, material also provides the advantage that the facing can be assembled with the frame essentially without trapping air between the parts because air can escape through the open-celled material. Further in case slurry is used to assemble the facing precursor and the frame to form a dental restoration precursor, components of the slurry may be enabled to escape through the open-celled material of the facing precursor. For example, because slurry may comprise liquid (for example for making the slurry workable or applicable to a desired surface) the liquid may evaporate through the open-celled material of the facing precursor. Therefore the time required to dry the slurry in a dental restoration precursor prior to sintering may be reduced by the present invention. Consequently, such a method has the advantage of providing a good bond between the facing and the frame because air and/or vapor (of the slurry), that could keep the mating parts at least partially separate, is minimized. Furthermore, because of the essential absence of air and/or vapor in the structure of the dental restoration, the strength and durability is very high.

An alternative method of making a facing for a dental restoration comprises the steps of:
  providing a blank of an organic material,
  forming a facing precursor from the blank, and
  forming a mold by use of the facing precursor.

The facing precursor may be used as a model or pattern to form a mold. Further, the facing precursor may be joined with a frame to form a pattern which is then used to form the mold. The mold may be used for preparing the final facing.

Consequently, the alternative method may comprise the step of molding a facing. Preferably the method of molding the facing includes the step of molding a facing on the frame. For example, the frame carrying the facing precursor may be used to form a mold cavity in a mold. The facing precursor may be removed from the mold by heating the mold together with the pattern so that the organic material the facing precursor is made of burns off. However, the heating temperature is typically selected so that the frame, which is typically made of ceramic material, remains in its shape, and thus forming a core of the mold. The space between frame and the mold, which was previously filled by the facing precursor, may now be filled with a flowable, for example molten, material like glass ceramic that is provided through an inlet channel of the mold. The material filled in the mold thereby may obtain the shape of the facing.

The flowable material preferably meets the frame inside of the mold, fuses to a surface of the frame and hardens to form the facing. Therefore the facing preferably is tightly attached to the frame, and in particular a surface of the facing fuses to a surface of the frame.

Preferably, the mold is a heat resistant dental casting material based on phosphate.

The organic material is preferably made from a completely burnable polymer material, meaning it contains essentially no inorganic fillers. Such organic materials may be, for example, polymethyl methacrylate (PMMA), or wax.

In an embodiment of the alternative method the step of forming a facing precursor from the blank comprises the step of machining. Preferably, the step of machining is performed on a CNC machine providing for automatic shaping of the facing precursor based on a data file. The step of machining may further comprise milling, laser cutting, and/or engraving.

The methods as they are described for the embodiments of the invention may as far as applicable be also used for the alternative method of making a facing.

BRIEF DESCRIPTION OF THE DRAWINGS

FIG. 1 is a schematic cross-sectional view of an example of a conventional process to prepare a facing for a dental restoration according to the Prior Art;

FIG. 3a, 3b are schematic cross-sectional views of an exemplary representation of a dental restoration according to an embodiment of the invention;

DETAILED DESCRIPTION

Figure 2:
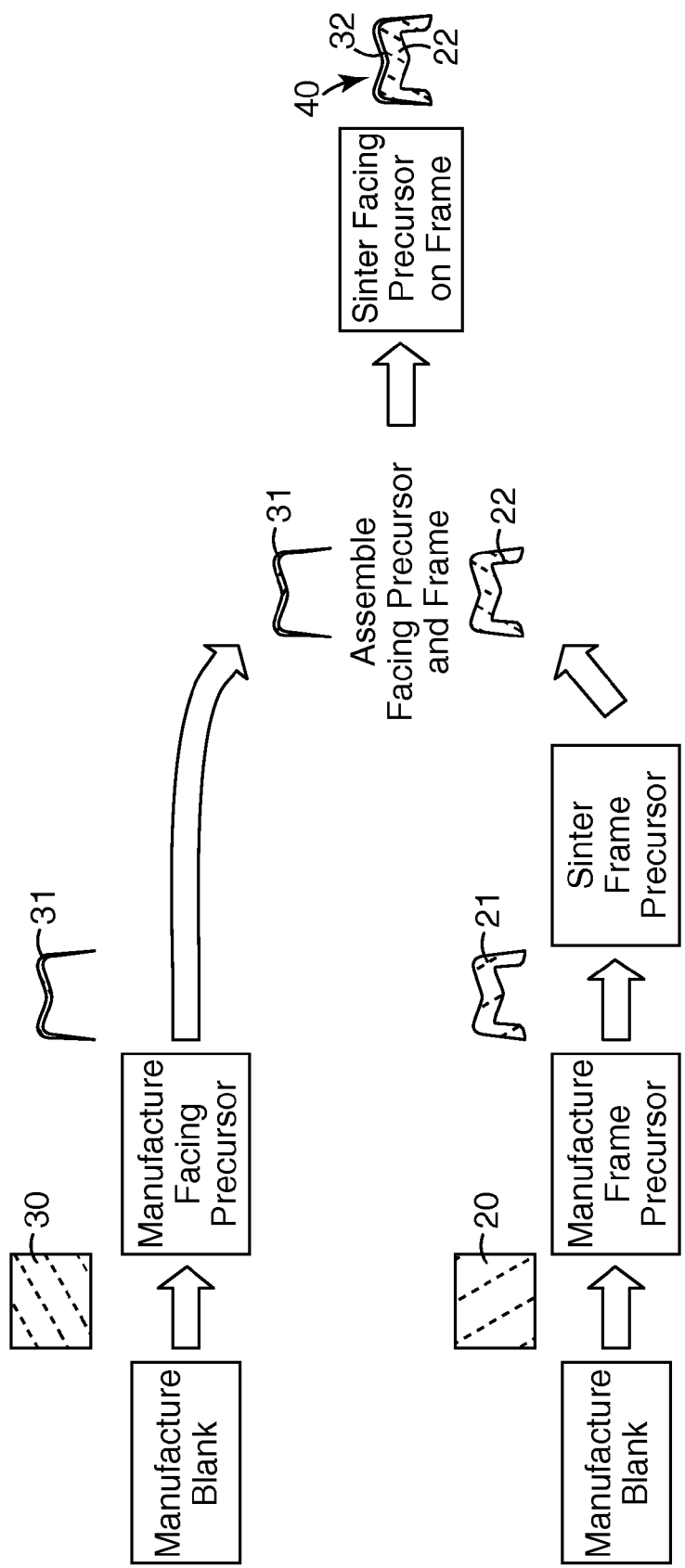
FIG. 2 is a flow diagram outlining an exemplary process for preparing a dental restoration according to an embodiment of the invention.

FIG. 2 gives an overview of an exemplary process to prepare a dental restoration according to an embodiment of the invention. Typically, the process starts with the preparation of the frame 22 made from a blank 20. The blank 20 is typically manufactured by pre-sintering a ceramic powder to form a machinable block for example according to a method as disclosed in EP 1712534 A1 and US 2006/0082033 A1. A frame precursor 21 is then machined from the blank 20 based on the desired shape of the frame 22, for example milled with a CNC milling machine. Finally the frame precursor 21 is usually sintered to form the frame 22.

The shape of the frame 22 may be designed with CAD software by an operator. The operator typically designs the frame 22 based on scan data obtained from capturing of a patient's teeth, for example by scanning a plaster model of the patient's teeth. It is also possible to make a model of the dental restoration and use the captured shape of the model for the design. Such model may, for example, be a wax model which is manually shaped by a dental technician. Alternatively, intra-oral scanning may be used, in which an image is captured directly from the patient's teeth, rather than from a model. These techniques are familiar to persons of skill in the field.

The preparation of the facing 32 will now be described. A blank 30 is provided made from an open-celled pre-sintered material from which a facing precursor 31 is formed. The facing precursor 31 is for example formed by milling it from the blank 30 with a CNC milling machine.

The shape of the facing precursor 31 may also be designed with CAD software. For example, the interior shape of the facing precursor may be designed based on the exterior shape of the frame 22, and the exterior shape of the facing precursor may be designed based on the exterior shape of the dental restoration 40. The shape of the frame 22 may be captured by scanning an available frame, or it may be available in the form of CAD data if the frame was designed with CAD software, for example. Further the shape of the frame 22 may be obtained partially or entirely from a database that includes standard frame shapes. The final shape of the dental restoration 40 may be designed based on a captured image or data set representing the shape of the patient's teeth, or based on a captured image or data set representing the shape of a model of the dental restoration, or based on shapes obtained from a library of images or data sets representing the shapes of various teeth.

On the basis of the shape of the frame and the shape of the final restoration the shape of the facing may be generated by the CAD system, so that the facing with its outer shape fits adjoining and cooperating teeth in the patient's mouth. Further, the shape of the facing is generated so that an inner surface of the facing fits with the outer shape of the frame.

The milled facing precursor 31 is then combined with the frame 22, and the facing-frame assembly is subsequently finally sintered to obtain the dental restoration 40. The sintering of the facing precursor 31 which is placed on the frame 22 is preferably performed at a temperature lower than the melting temperature of the frame 22, so that the frame 22 substantially maintains its shape and mechanically supports the facing precursor 31 that is softened during sintering.

Because the facing precursor typically shrinks during sintering the shape of the facing precursor usually is proportionally enlarged relative to the shape of the final facing. Alternatively, the facing 32 is sintered before it is combined with a sintered frame (diagram of the alternative not shown). In this case the facing precursor is milled to substantially its final shape.

The dental restoration 40 may be finally shaped, could be sandblasted and/or the surface may be at least partially finished with glaze.

FIGS. 3a and 3b are schematic cross-sectional views showing an exemplary representation of a dental restoration that includes a crown 4 made from a frame 2 and a facing 3. FIG. 3a illustrates the assembly of the crown 4 onto to a prepared natural tooth 1. The natural tooth 1 is prepared so that it consists essentially of healthy tooth substance and provides a solid support for receiving the crown 4. This preparation is typically done by removing any caries-infected tooth substance, and shaping the tooth by grinding to create a structure allowing for the support of and bonding to a dental restoration. The crown 4 is then assembled on the prepared tooth by mating opposed surfaces of the crown 4 with the surfaces of the prepared tooth 1. FIG. 3b shows the restored tooth. The crown 4 is affixed to the natural tooth 1, for example, with adhesive cement of the type available from 3M ESPE Dental of Seefeld, Germany, under the designation Ketac™ Cem Plus.

Figure 4A:
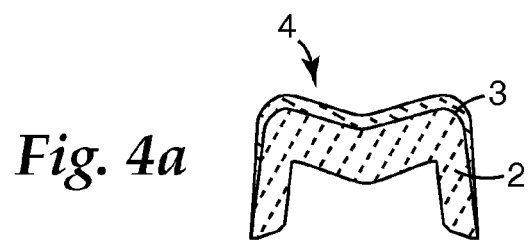
FIGS. 4a-4e are diagrams showing various representations of a dental restoration to which the invention is applicable according to an embodiment of the invention.
Figure 4B:
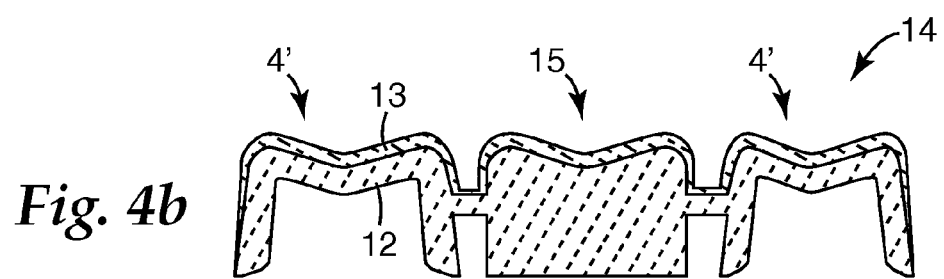

As shown in FIGS. 4a-4e, the dental restoration may be used to replace natural tooth substance to different extents, up to replacing an entire tooth or several teeth. FIG. 4a again shows crown 4 of FIG. 3 with the frame 2 and the facing 3. FIG. 4b shows a bridge 14 that basically consists of two crowns 4' connected with a pontic 15 that is designed to replace an entire absent tooth. The bridge has a frame 12 and attached to it a facing 13 prepared and applied in accordance with the invention. Therefore the bridge 14 spans an area where a natural tooth is missing. Typically a bridge extends from a prepared natural tooth, to a pontic, and then to another prepared natural tooth. A bridge can also be designed to replace two or more missing teeth, for example by including two or more pontics connected to each other in the same manner as the single pontic described above. A bridge may also have only one crown attached to only one natural tooth, for example in case a second natural tooth is not available or not suitable for attachment.

Figure 4C:
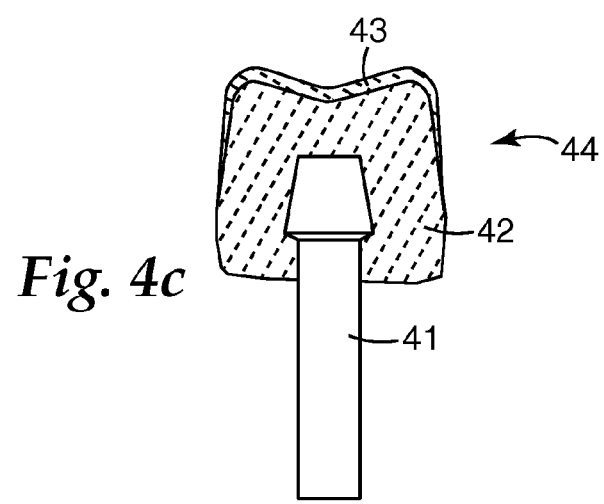

FIG. 4c shows as a further example of a dental restoration an abutment 44 having a facing 43 and a frame 42 prepared and applied in accordance with the invention. The abutment 44 is attached on a dental implant 41 that, for example, may be implanted in a patient's jaw. An abutment typically replaces an entire natural tooth and may be an alternative to a bridge. As an advantage relative to a bridge the abutment does not require the preparation of adjoining natural teeth and therefore helps to maintain the patient's natural teeth. An abutment may also replace two or more natural teeth and may be attached to two or more dental implants 41, however preferably two implants may provide sufficient fixation of an abutment replacing more than two teeth. The abutment may be connected with a pontic or may be part of a bridge, for example a bridge that extends from a dental implant, includes a pontic, and is connected to a crown that is bonded to a prepared tooth. Such a bridge may also have more than one pontic.

Figure 4D:
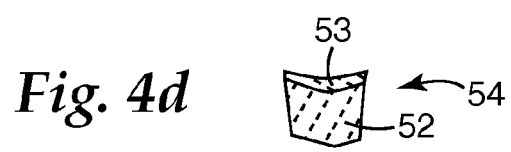
Figure 4E:
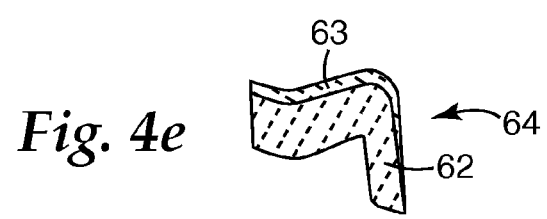

Finally, FIG. 4d shows an inlay 54 with a facing 53 attached to a frame 52, and FIG. 4e shows an onlay 64 with facing 63 attached to a frame 62 as further examples. The facings 53, 63 are prepared and applied in accordance with the invention. Inlays and onlays are typically used as smaller dental restorations. Typically an inlay replaces a part of an occlusal surface of a tooth and an onlay in addition replaces at least one side surface of a tooth. Inlays and onlays are typically alternatives to dental fillings, and are made for example of hardenable filling materials. They usually provide better aesthetic characteristics and better durability than normal filling materials.

Although specific embodiments of the present invention have been described above in detail, it will be understood that this description is merely for purposes of illustration. Various modifications of and equivalents corresponding to the disclosed aspects of the preferred embodiments described above may be made by those skilled in the art without departing from the spirit of the present invention, which is defined by the following claims.

Example 1

A zirconia frame for a first upper human molar crown has been manufactured by milling a pre-sintered blank of Lava™ Frame Crown using a milling machine available under the designation Lava™ Form from 3M ESPE AG, Germany. The frame has been sintered with a heating rate of 10 Kelvin per minute up to a temperature of about 1500° C. and a dwell time of about 120 minutes. The finished frame had a density of about 6.07 g/cm$^3$.

A facing precursor for a first upper human molar crown was milled out of a blank of pre-sintered and open-celled commercially available glass ceramic material using the Lava™ Form milling machine. The blank was uniaxially pressed from a powder of a glass ceramic material as specified below. The pressed blank had a pressed density which was in the range of about 1.34 g/cm$^3$ and about 1.42 g/cm$^3$. The pressed blank was pre-sintered at ambient pressure of about 101.3 kPa in a process that comprised the steps of:

(1) exposing the blank to a temperature that was increased from room temperature of about 23° C. to about 540° C. at a heating rate of about 10 Kelvin per minute;
(2) exposing the blank to the temperature of about 540° C. for a dwell time period of about 30 minutes;
(3) exposing the blank to a temperature that was increased from the temperature of about 540° C. to a temperature of 580° C. at a heating rate of about 10 Kelvin per minute; and
(4) exposing the blank to the temperature of about 580° C. for a dwell time period of about 30 minutes.

The blank was made of the reference glass ceramic material as specified herein.

The facing precursor and the frame have been assembled with an amount of slurry arranged between. The slurry was prepared from the same glass ceramic powder as used for the facing precursor which was mixed with a liquid comprising about 0.9900% by weight poliglykol 4000 P (available from Clariant, under the Prod. code 109467), about 49.50% by weight 1,2-Propandiol (available from Eissler Sientific) and de-ionized water ad to 100% by weight. The (glass ceramic) powder to liquid ratio was about 2:1 by weight. This slurry was applied to both parts with a slight surplus eventually needed for filling a gap between the facing precursor and the frame.

The so formed dental restoration precursor was dried at a drying temperature of about 60° C. for a drying time of about 3 minutes and then moved into a chamber of a furnace that was preheated to about 400° C. The time required for moving the dental restoration precursor into the furnace chamber was about another 3 minutes in which the dental restoration precursor was initially exposed to the drying temperature, and finally to the 400° C. present in the furnace chamber. The furnace chamber then was heated to the sintering temperature of about 790° C. at a heating rate of about 45 Kelvin per minute. During the heating time period (the time period in which the temperature was increased to the sintering temperature) the furnace was evacuated from an initial ambient pressure of about 101.3 kPa to about 35 kPa. After the heating time period the dental restoration was exposed to the sintering temperature of about 790° C. for a dwell time of about 1 minute under ambient pressure of about 101.3 kPa. The sintering temperature of 790° C. was selected in accordance with the melting point of the material used for the facing precursor.

In the example a sintering furnace was used which is available under the designation "Dekema Austromat 3001" from Dekema Dental Keramikofen GmbH, Freilassing, Germany.

Comparative Example 1.1

A zirconia frame for a first upper human molar crown has been manufactured by milling a pre-sintered blank of Lava™ Frame Crown using the Lava™ Form milling machine. The frame has been sintered with a heating rate of 10 Kelvin per minute up to a temperature of about 1500° C. and a dwell time of about 120 minutes. The finished frame had a density of about 6.07 g/cm$^3$.

A facing precursor for a first upper human molar was manufactured by grinding an "E-max cad block LT A1/C14" supplied by Ivoclar Vivadent AG, Schaan, Liechtenstein in a Cerec Inlab supplied by Sirona AG, Bensheim, Germany.

The facing precursor and the frame have been assembled with an amount of slurry arranged between. The slurry was prepared from a glass ceramic powder available under the designation "Empress Add-On powder" from the Ivoclar Vivadent AG, Schaan, Liechtenstein and a liquid available under the designation "E-max ceram buildup fluid all-round" from the Ivoclar Vivadent AG, Schaan, Liechtenstein. The powder to liquid ratio was about 2:1 by weight.

This slurry was applied to both parts with a slight surplus eventually needed for filling a gap between the facing precursor and the frame.

The so formed dental restoration precursor was dried at a drying temperature of about 60° C. for a drying time of about 3 minutes and then moved into a chamber of a furnace that was preheated to about 400° C. The time required for moving the dental restoration precursor into the furnace chamber was about another 3 minutes in which the dental restoration precursor was initially exposed to the drying temperature, and finally to the 400° C. present in the furnace chamber. The furnace chamber then was heated to the sintering temperature of about 850° C. at a heating rate of about 45 Kelvin per minute. During the heating time period (the time period in which the temperature was increased to the sintering temperature) the furnace was evacuated from an initial ambient pressure of about 101.3 kPa to about 35 kPa. After the heating time period the dental restoration was exposed to the sintering temperature of about 850° C. for a dwell time of about 1 minute under ambient pressure of about 101.3 kPa. The sintering temperature of 850° C. was selected in accordance with the melting point of the material used for the facing precursor.

For this and the further comparative examples the same sintering furnace as in example 1 was used ("Dekema Austromat 3001" from Dekema Dental Keramikofen GmbH, Freilassing, Germany).

Comparative Examples 1.2

Comparative Example 1.1 was repeated using the same type of materials and in the same way, but in Comparative Example 1.2 with a drying time of about 6 minutes rather than 3 minutes.

Comparative Example 2.1

Example 1 was repeated, but with the facing precursor obtained from previously sintered material. Therefore the frame and the facing precursor were prepared from the same type of material and in the same way as in Example 1. However, the facing precursor had a material structure that was generally free of cells prior to assembly with the frame. Thus the material structure of the facing precursor prior to assembly to the frame was outside the range of an open-celled material as referred to in this specification.

The facing precursor was made from a blank that was sintered in a process that comprised the steps of:
(1) exposing the blank to a temperature that was increased from room temperature of about 23° C. to about 540° C. at a heating rate of about 10 Kelvin per minute at ambient pressure of about 101.3 kPa;
(2) exposing the blank to the temperature of about 540° C. for a dwell time period of about 30 minutes at ambient pressure of about 101.3 kPa;
(3) exposing the blank to a temperature that was increased from the temperature of about 540° C. to about 800° C. at a heating rate of about 10 Kelvin per minute at reduced pressure of about 35 kPa; and
(4) exposing the blank to the temperature of about 800° C. for a dwell time period of about 30 minutes at ambient pressure of about 101.3 kPa.

The obtained blank was glued on a stub so that it could be processed on the Cerec InLab machine available from Sirona AG, Bensheim, Germany. The facing precursor then was machined from the blank by grinding, assembled to the frame, and the so-formed dental restoration precursor was sintered. The assembly and the sintering process were conducted in accordance to Example 1.

In Comparative Example 2.1 a drying time of 3 minutes was used.

Comparative Examples 2.2, 2.3

In Comparative Example 2.2 the Comparative Example 2.1 was repeated with a drying time of 6 minutes rather than 3 minutes, and in Comparative Example 2.3 with a drying time of 9 minutes.

Results of the Comparative Examples 1.1, 1.2, 2.1, 2.2 and 2.3 relative to Example 1

Figure 5:
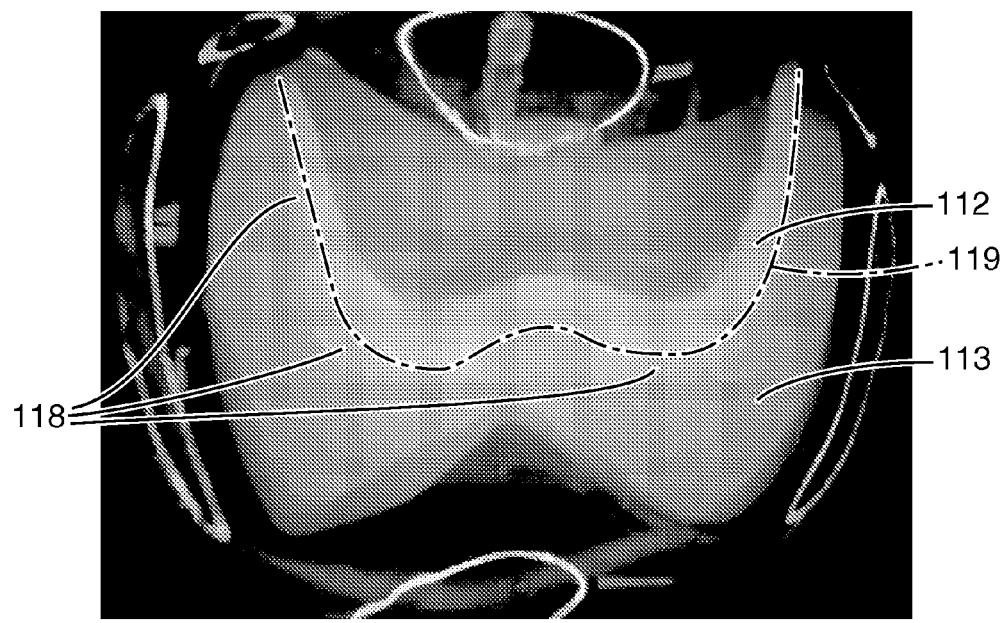
FIGS. 5, 6 are photographs of cross-sections of dental restorations manufactured according to Comparative Examples 1.1 and 1.2 of this specification.

FIG. 5 shows a cross-section of a dental restoration which was manufactured according to Comparative Example 1.1. The figure shows a frame 112 and a facing 113 which are joined as approximately indicated by line 119. Reference number 118 depicts exemplary areas in the dental restoration which comprise a defective material structure. In this case such defective material structure comprises cracks and voids that appear as bright patterns in the photograph.

Figure 6:
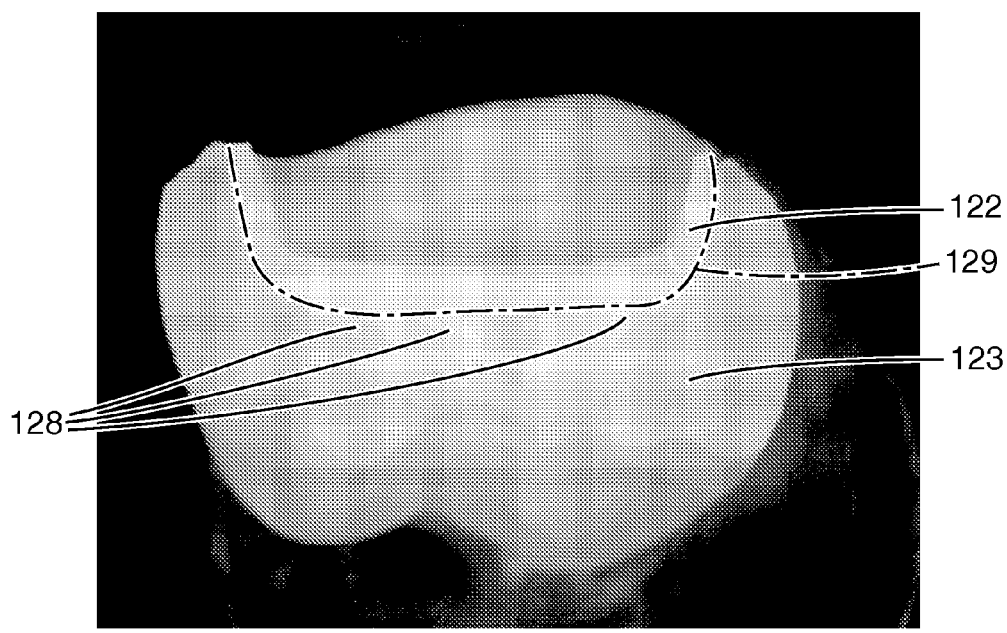

FIG. 6 shows a cross-section of a dental restoration which was manufactured according to Comparative Example 1.2. The line 129 again indicates the area at which a frame 122 joins with a facing 123. Also in this example the dental restoration has areas of defective material structure which comprises cracks and voids, again visible as bright areas. Some areas of defective material structure are by way of example depicted by reference number 128.

As can be seen from FIGS. 5 and 6 the defective areas are located adjacent joint 118, 128 between the frame 112, 122 and the facing 113,123, respectively.

Figure 7:
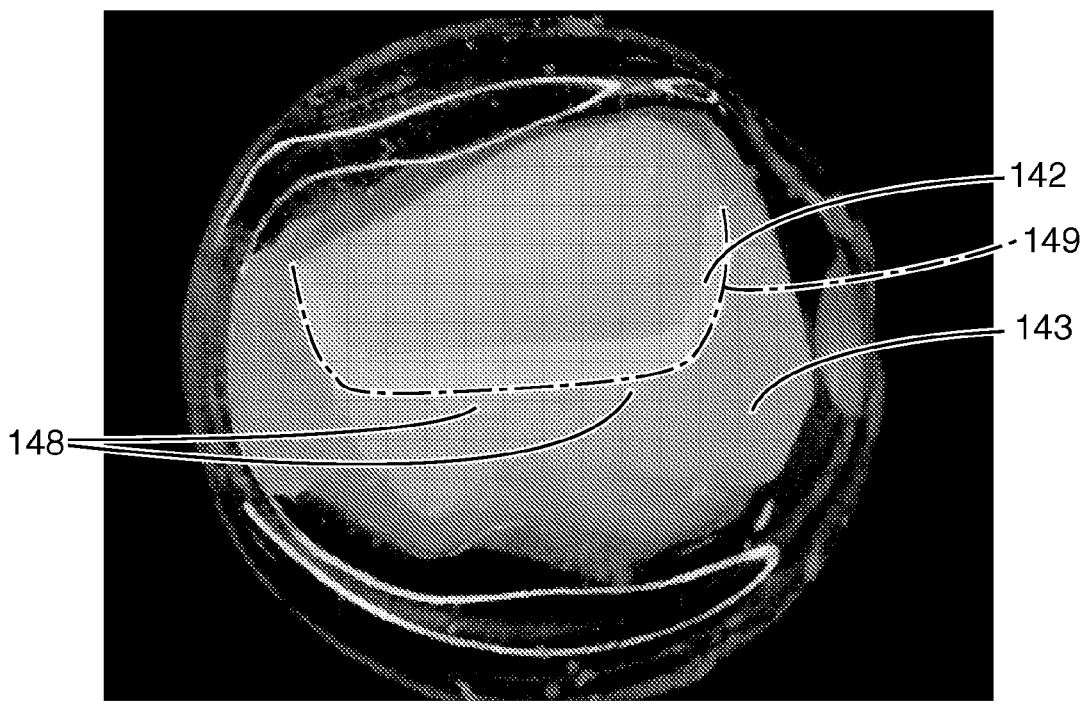
FIGS. 7, 8 are photographs of cross-sections of dental restorations manufactured according to Comparative Examples 2.1-2.2 of this specification.

FIG. 7 shows a cross-section of a dental restoration which was manufactured according to Comparative Example 2.1. Similar to the examples shown in FIGS. 5 and 6 also the dental restoration shown in FIG. 7 has areas of defective material structure, for example indicated by reference number 148. Such areas again are located adjacent a joint between a frame 142 and a facing 143.

Figure 8:
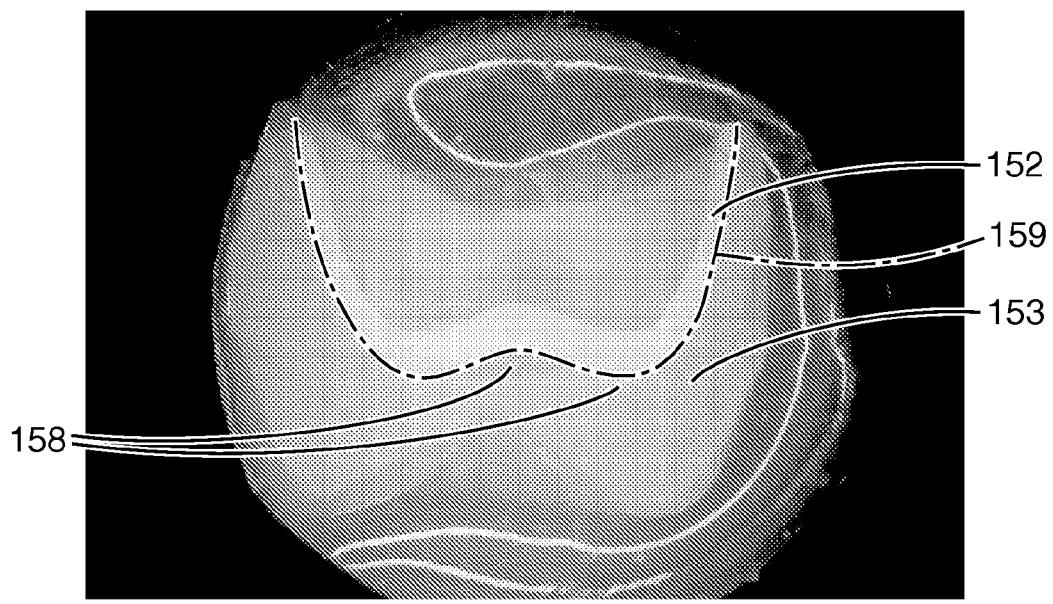

Further FIG. 8 shows a cross-section of a dental restoration which was manufactured according to Comparative Example 2.2, with a frame 152, a facing 153 and a joint between the frame 152 and the facing 153, approximately indicated by line 159. FIG. 8 also shows defective areas, for example as depicted by reference number 158.

Figure 9:
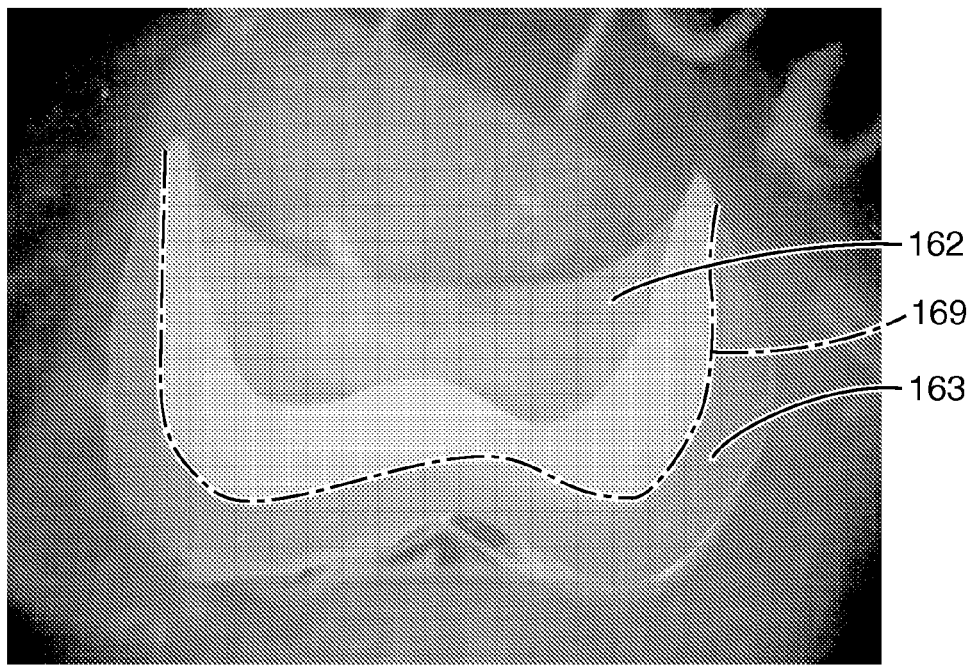
FIG. 9 is a photograph of a cross-section of dental restoration manufactured according to Examples 1 of this specification.

FIG. 9 shows a cross-section of a dental restoration which was manufactured according to Example 1. The dental restoration shown appeared to be substantially free of defective areas. The transition (approximately indicated by line 169) between the frame 162 and a facing 163 appeared to be generally free of voids.

Figure 10:
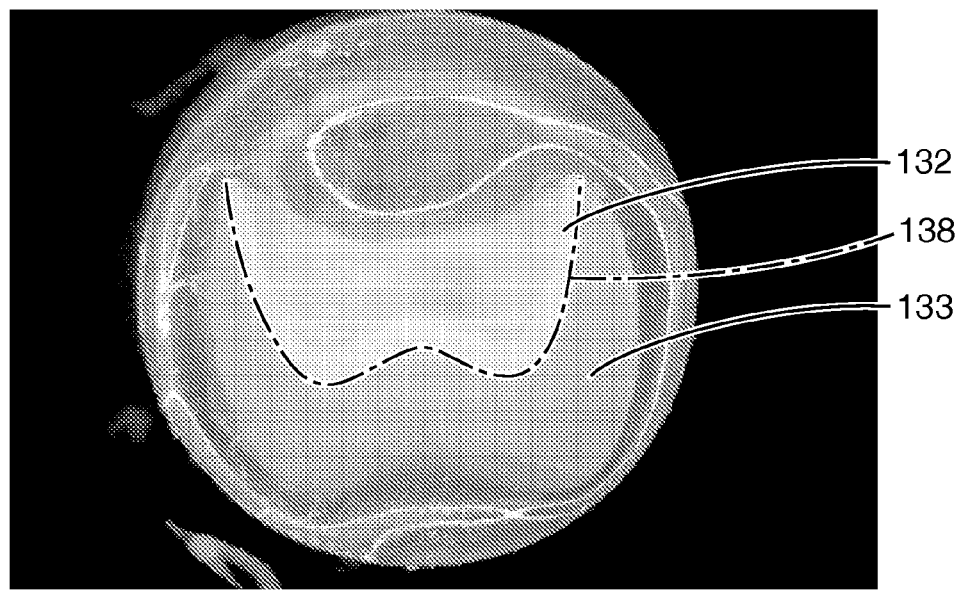
FIG. 10 is a photograph of a cross-section of dental restoration manufactured according to Comparative Example 2.3 of this specification.

FIG. 10 shows a cross-section of a dental restoration which was manufactured according to Comparative Example 2.3. A frame 132 joins with a facing 133 in the proximity of line 138. The dental restoration shown appeared to have less defective areas than the dental restorations shown in FIGS. 5 to 8.

Figure 11:
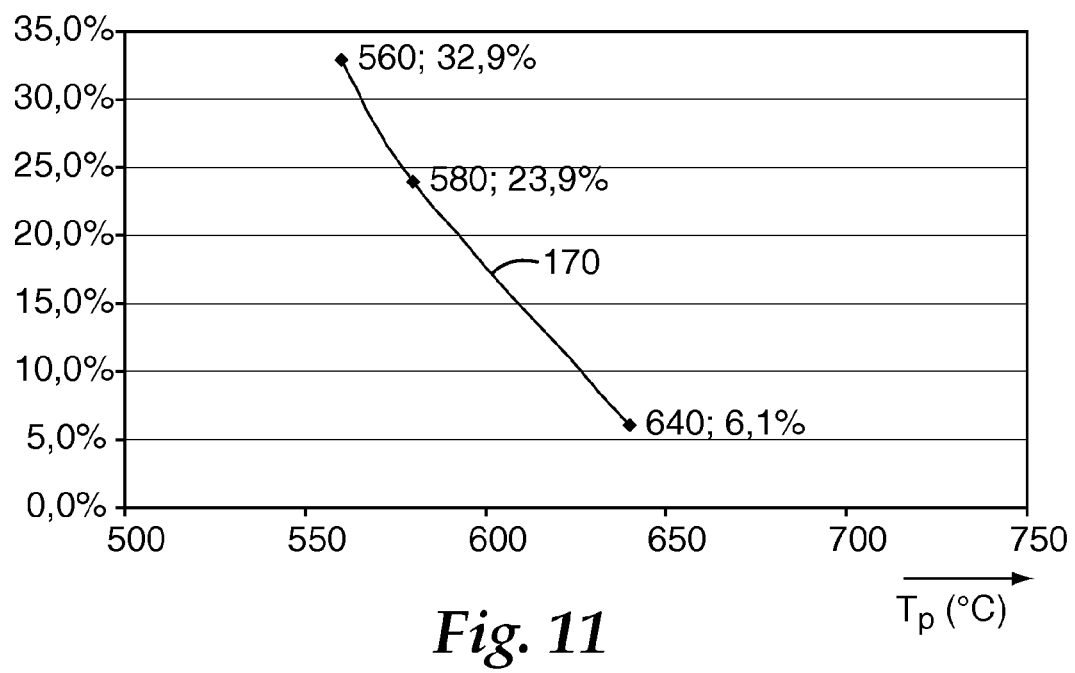
FIG. 11 is a diagram representing data measured at a reference glass ceramic material by use of the mercury porosimetry according to DIN 66133.

FIG. 11 is a diagram representing along the vertical axis the porosity or open porosity according to the mercury porosimetry as specified in DIN 66133. Along the horizontal axis a maximum pre-sintering temperature $T_p$ is represented. The diagram further shows a curve 170 that is based on measurements of the porosity or open porosity depending on the pre-sintering temperature $T_p$. The pre-sintering temperature referred to in the diagram is the maximum temperature at which samples used for the measurements were pre-sintered. The samples used were uniaxially pressed from a powder of the reference glass ceramic material as specified herein. The pressed samples had a pressed density which was in the range of about 1.34 g/cm³ and about 1.42 g/cm³. Each pressed sample was pre-sintered at ambient pressure of about 101.3 kPa in a process that comprised the steps of:
(1) exposing the sample to a temperature that was increased from room temperature of about 23° C. to about 540° C. at a heating rate of about 10 Kelvin per minute;
(2) exposing the sample to the temperature of about 540° C. for a dwell time period of about 30 minutes;
(3) exposing the sample to a temperature that was increased from the temperature of about 540° C. to the pre-sintering temperature $T_p$ (as represented in the diagram) at a heating rate of about 10 Kelvin per minute; and
(4) exposing the sample to the temperature of about the maximum temperature $T_p$ for a dwell time period of about 30 minutes.

CONCLUSIONS

FIG. 9, based on Example 1, shows a dental restoration which appeared to be substantially free of defective areas adjacent the joint between the frame and the facing. FIGS. 5 to 8, based on the Comparative Examples, in contrast show such defective areas.

One substantial difference between the Example 1 (FIG. 9) and the Comparative Examples 1.1, 1.2 (FIGS. 5, 6) is the facing precursor being comprised of an open-celled material in Example 1, whereas in the Comparative Examples the facing precursor is made of a material that is generally free of cells, or at least is comprised of or consists of a closed-celled material structure.

Another substantial difference between the Example 1 (FIG. 9) and the Comparative Examples 1.1, 1.2 (FIGS. 5, 6) is the type of material used for the facing (or the facing precursor). On the other hand, Comparative Examples 2.1, 2.2 generally correspond to Comparative Examples 1.1, 1.2 respectively, but with Comparative Examples 2.1, 2.2 using the same type of material like Example 1. The substantial difference between the Example 1 and the Comparative Examples 2.1, 2.2 (FIGS. 7, 8), is the facing precursor being comprised of an open-celled material in Example 1, whereas in the Comparative Examples the facing precursor is made of a material that is generally free of cells, or at least is comprised of or consists of a closed-celled material structure. Therefore it is believed that the open-celled structure of the facing precursor rather than the type of material contributes to achieve a dental restoration being substantially free of defective areas.

It is believed that in Example 1 components of the slurry (for example the liquid) used for assembly of the facing precursor and the frame can escape through the open-celled material during drying, and probably at the beginning of the sintering process. It is further assumed that components of the slurry if trapped within the dental restoration may cause defective areas as shown in FIGS. 5 to 8, but not visible in FIG. 9.

Support may be given by Comparative Example 2.3 (FIG. 10) in which a long drying time may have caused components of the slurry to escape prior to sintering the dental restoration precursor. The example shown in FIG. 10 shows a dental restoration that is generally free of defects which may be a result of the long drying time that may have enabled the liquid of the slurry to escape prior to sintering.

Therefore another conclusion may be that the drying time may be reduced due to the facing precursor being comprised of an open-celled material.

It was also found that as an advantage a facing precursor comprised of an open-celled material may help to reduce the milling time because milling of a sintered glass ceramic tended to cause chippings at the facing precursor so that the milling speed preferably would be reduced to avoid such chippings.

The invention claimed is:

1. A method of making a dental restoration precursor, comprising the step of:
providing a facing precursor from which a facing is obtainable,
providing a blank of an open-celled, pre-sintered material,
forming an open-celled, pre-sintered facing precursor from the blank, and
mating the open-celled, pre-sintered facing precursor with a closed-celled, sintered frame to form a dental restoration precursor.

2. The method of claim 1, further comprising the step of sintering the pre-sintered facing precursor to form the facing.

3. The method of claim 2, wherein the facing precursor has a first material density and the facing has a second material density, wherein the second material density is higher than the first material density.

4. The method of claim 3, wherein the second material density is in a range of 2 g/cm³ to 2.7 g/cm³, and the first material density is in a range of 30% to 92% of the second material density.

5. The method of any one of claims 1, and 2-4, wherein the facing comprises a glass ceramic material.

6. The method of any one of claims 1, and 2-4, wherein the facing precursor is proportionally enlarged relative to the facing by a magnification factor of between 1.12 to 1.17.

7. The method of claim 2, wherein sintering results in the facing precursor shrinking proportionally.

8. The method of claim 1, wherein providing forming the facing precursor from the blank includes machining.

9. The method of claim 8, wherein machining includes one or both selected from grinding and milling.

10. The method of claim 9, comprising the steps of:
forming an exterior surface of the facing precursor based on a virtual model of an exterior surface of the dental restoration; and
forming an interior surface of the facing precursor based on a virtual model of an exterior surface of a frame.

11. The method of claim 10, further comprising the step of modeling the exterior surface of the dental restoration on a CAD system.

12. The method of claim 10, wherein forming of the exterior surface of the facing precursor includes at least one procedure selected from scanning a patient's tooth, scanning a temporary restoration, and scanning a model of a patient's tooth.

13. The method of claim 1, further comprising the step of heating the dental restoration precursor and thereby sintering at least the facing precursor.

14. The method of claim 1, wherein heating of the dental restoration precursor fuses a surface of the facing to a surface of the frame.

15. The method of claim 10, further comprising the step of at least partially glazing the facing.

16. Dental restoration precursor, comprising a frame and a facing prepared according to the method of claim 1.

17. The method of claim 1, wherein providing a pre-manufactured facing precursor comprises the step of:
- controlling a CNC machine based on data related to the shape of the facing precursor which are obtained from a CAD system, wherein the facing precursor is proportionally enlarged with respect to the facing.

18. A method of making a dental restoration precursor, comprising the step of:
- providing a facing precursor from which a facing is obtainable,
  - providing a blank of an open-celled, pre-sintered material,
  - forming an open-celled, pre-sintered facing precursor from the blank, and
- providing a closed-celled, sintered frame,
- providing a ceramic slurry comprising a powdery glass ceramic material mixed with water, and
- mating the open-celled, pre-sintered facing precursor and the closed-celled, sintered frame with the ceramic slurry arranged between mated surfaces of the frame and the facing precursor to form a dental restoration precursor.

19. The method of claim 18, further comprising the step of
- sintering the pre-sintered facing precursor to form the facing and fuse the facing to the frame.

* * * * *

UNITED STATES PATENT AND TRADEMARK OFFICE
CERTIFICATE OF CORRECTION

| | |
|---|---|
| PATENT NO. | : 9,579,172 B2 |
| APPLICATION NO. | : 12/599995 |
| DATED | : February 28, 2017 |
| INVENTOR(S) | : Bernd Burger |

It is certified that error appears in the above-identified patent and that said Letters Patent is hereby corrected as shown below:

In the Specification

Column 3
Line 11, delete "of Preferably" and insert -- of, preferably --, therefor.

Column 10
Line 64, delete "mm²'" and insert -- $mm^2$. --, therefor.

Column 11
Line 1, delete "40 nm." and insert -- 40 μm. --, therefor.

Column 16
Line 13, delete "poliglykol" and insert -- polyglykol --, therefor.

Column 16
Line 15, delete "Sientific)" and insert -- Scientific) --, therefor.

In the Claims

Column 20
Line 40, in Claim 8, delete "wherein providing" and insert -- wherein --, therefor.

Signed and Sealed this
Third Day of October, 2017

Joseph Matal
*Performing the Functions and Duties of the*
*Under Secretary of Commerce for Intellectual Property and*
*Director of the United States Patent and Trademark Office*